United States Patent [19]

Glover et al.

[11] Patent Number: 4,994,744
[45] Date of Patent: Feb. 19, 1991

[54] METHOD FOR COMBINING ACQUIRED NMR DATA TO SUPPRESS MOTION ARTIFACTS

[75] Inventors: Gary H. Glover, Menlo Park, Calif.; Stephen W. Flax, Wauwatosa, Wis.

[73] Assignee: General Electric Company, Milwaukee, Wis.

[21] Appl. No.: 499,235

[22] Filed: Mar. 26, 1990

Related U.S. Application Data

[63] Continuation-in-part of Ser. No. 401,374, Aug. 31, 1989, abandoned, and a continuation-in-part of Ser. No. 427,401, Oct. 27, 1989, and Ser. No. 401,374, Aug. 31, 1989, abandoned.

[51] Int. Cl.$^5$ .............................................. G01R 33/20
[52] U.S. Cl. ..................................... 324/309; 324/306
[58] Field of Search ............... 324/300, 306, 307, 309, 324/310, 311, 312, 313, 314, 318, 322; 128/653 A, 653 AF

[56] References Cited

U.S. PATENT DOCUMENTS

| | | | |
|---|---|---|---|
| 4,734,646 | 3/1988 | Shenoy | 324/309 |
| 4,849,697 | 7/1989 | Cline | 324/306 |
| 4,896,113 | 1/1990 | Pelc | 324/312 |

Primary Examiner—Michael J. Tokar
Attorney, Agent, or Firm—Quarles & Brady

[57] ABSTRACT

Displacement values which indicate respiration phase are acquired along with each view of an NMR scan. Two or more such NMR scans are conducted and the deviation of each displacement value from a smooth reference curve is employed to measure the integrity of its associated NMR image data. The NMR image data from the separate scans are combined to reduce random noise and motion artifacts, and the combination is accomplished by weighting the data in accordance with its measured integrity.

5 Claims, 4 Drawing Sheets

METHOD FOR COMBINING ACQUIRED NMR DATA TO SUPPRESS MOTION ARTIFACTS

RELATED APPLICATIONS

This application is a continuation-in-part of U.S. patent application Ser. No. 401,374 filed on Aug. 31, 1989 now abandoned and a continuation-in-part of U.S. patent application Ser. No. 427,401 filed on Oct. 27, 1989.

BACKGROUND OF THE INVENTION

This invention relates to nuclear magnetic resonance imaging methods. More specifically, this invention relates to a method for controlling image artifacts caused by substantially periodic NMR signal variations due, for example, to subject motion in the course of an NMR scan.

NMR has been developed to obtain images of anatomical features of human patients. Such images depict nuclear spin distribution (typically, protons associated with water and tissue), spin-lattice relaxation time $T_1$, and/or spin-spin relaxation time $T_2$ and are of medical diagnostic value. NMR data for constructing images can be collected using one of many available techniques, such as multiple angle projection reconstruction and Fourier transform (FT). Typically, such techniques comprise a pulse sequence made up of a plurality of sequentially implemented views. Each view may include one or more NMR experiments, each of which comprises at least an RF excitation pulse and a magnetic field gradient pulse to encode spatial information into the resulting NMR signal. As is well-known, the NMR signal may be a free induction decay (FID) or, preferably, a spin-echo signal.

The preferred embodiments of the invention will be described in detail with reference to a variant of the well known FT technique, which is frequently referred to as "spinwarp". It will be recognized, however, that the method of the invention is not limited to FT imaging methods, but may be advantageously practiced in conjunction with other techniques, such as multiple angle projection reconstruction disclosed in U.S. Pat. No. 4,471,306, and another variant of the FT technique disclosed in U.S. Pat. No. 4,070,611. The spin-warp technique is discussed in an article entitled "Spin Warp NMR Imaging and Applications to Human Whole Body Imaging" by W. A. Edelstein et al., *Physics in Medicine and Biology*, Vol. 25, pp. 751-756 (1980).

Briefly, the spin-warp technique employs a variable amplitude phase encoding magnetic field gradient pulse prior to the acquisition of NMR spin-echo signals to phase encode spatial information in the direction of this gradient. In a two-dimensional implementation (2DFT), for example, spatial information is encoded in one direction by applying a phase-encoding gradient ($G_y$) along that direction, and the observing a spin-echo signal in the presence of a second magnetic field gradient ($G_x$) in a direction orthogonal to the phase-encoding direction. The $G_x$ gradient present during the spin-echo encodes spatial information in the orthogonal direction. In a typical 2DFT pulse sequence, the magnitude of the phase-encoding gradient pulse $G_y$ is incremented ($\Delta G_y$) monotonically in the sequence of views that are acquired to produce a set of NMR data from which an entire image can be reconstructed.

Object motion during the acquisition of NMR image data produces both blurring and "ghosts" in the phase-encoded direction. Ghosts are particularly apparent when the motion is periodic, or nearly so. For most physiological motion, including cardiac and respiratory motion, each view of the NMR signal is acquired in a period short enough that the object may be considered stationary during the acquisition window. Blurring and ghosts, therefore, are due primarily to the inconsistent appearance of the object from view to view, and in particular, due to changes in the amplitude and/or phase of the NMR signal due to the motion.

Both blurring and ghosts can be reduced if the data acquisition is synchronized with the functional cycle of the object. This method is known as gated NMR scanning, and its objective is to acquire NMR data at the same point during successive functional cycles so that the object "looks" the same in each view. The drawback of gating is that NMR data may be acquired only during a small fraction of the object's functional cycle, and even when the shortest acceptable pulse sequence is employed, the gating technique can significantly lengthen the data acquisition time.

One proposed method for eliminating ghost artifacts is disclosed in U.S. Pat. No. 4,567,893, issued on Feb. 4, 1986, and is assigned to the same assignee as the present invention. In this prior application, it is recognized that the distance in the image between the ghosts and the object being imaged is maximized when the NMR pulse sequence repetition time is an odd multiple of one-fourth of the duration of the periodic signal variation (if two phase-alternated RF excitation pulses per view are used, as disclosed and claimed in commonly assigned U.S. Pat. No. 4,443,760, issued Apr. 17, 1984). It is recognized that this ratio can be used to alleviate ghosts due to respiratory motion. While this method, indeed, improves image quality, it does impose a constraint on the NMR pulse sequence repetition time and it often results in a longer total scan time. It also assumes that the motion is periodic. Its effectiveness is diminished when the subject's breathing is irregular because the ghosts are blurred and can overlap the image.

Another method for reducing the undesirable effects due to periodic signal variations is disclosed in U.S. Pat. No. 4,706,026 issued Nov. 10, 1987 and entitled "A Method For Reducing Image Artifacts Due To Periodic Variations In NMR Imaging." In one embodiment of this method, an assumption is made about the signal variation period (e.g. due, for example, to patient respiration) and the view order is altered from the usual monotonically increasing phase-encoding gradient to a preselected order. This involves establishing the order in which either the gradient parameters, i.e. the amplitude of the phase-encoding gradient pulses (in the spin-warp method) or the direction of the read-out gradient pulses (in the multiple angle projection reconstruction method) are implemented. For a given signal variation period, a view order is chosen so as to make the NMR signal variation as a function of the phase-encoding amplitude (or gradient direction) be at a desired frequency. In one embodiment, the view order is selected such that the variation period appears to be equal to the total NMR scan time (low frequency) so that the ghost artifacts are brought as close to the object being imaged as possible. In another embodiment (high frequency), the view order is chosen to make the variation period appear to be as short as possible so as to push the ghost artifacts as far from the object as possible.

This prior method is effective in reducing artifacts, and is in some respects ideal if the variation is rather regular and at a known frequency. On the other hand, the method is not very robust if the assumption made about the motion temporal period does not hold (e.g., because the patient's breathing pattern changes or is irregular). If this occurs, the method loses some of its effectiveness because the focusing of the ghosts, either as close to the object or as far from the object as possible, becomes blurred. A solution to this problem is disclosed in U.S. Pat. No. 4,663,591 entitled "A Method For Reducing Image Artifacts Due To Periodic Signal Variations in NMR Imaging." In this method, the non-monotonic view order is determined as the scan is executed and is responsive to changes in the period so as to produce a desired relationship (low frequency or high frequency) between the signal variations and the gradient parameter.

While the above described methods reduce motion artifacts, they do rely on some regularity, or predictability, in the cyclic motion which is not always present. For example, irregularities may occur during a breathing cycle which introduces errors into the data acquired for one or more views of the scan. One method for reducing such spurious errors is to perform two scans, or acquire twice the necessary data during a single scan and then average the information acquired for each view to produce an image of increased quality.

SUMMARY OF THE INVENTION

The present invention relates to an improved method and system for combining redundant NMR data for the purpose of reducing artifacts caused by patient motion. More specifically, the invention includes means for acquiring a plurality of sets of NMR image data, acquiring with each set of image data an associated set of motion data that indicates displacement of the subject during each view of acquired image data; means for generating a smooth reference curve for each set of acquired motion data; means for determining the deviation of the acquired motion data from its reference curve; and combining the NMR image data for each view in the two sets of NMR image data as a function of the deviation of its associated motion data. Rather than merely averaging the redundant data for each view, the present invention contemplates giving more weight to data which is more likely to provide reduced motion artifacts in the image, based on the deviation of its associated motion data from the reference curve.

A general object of the invention is to reduce motion artifacts by intelligently combining redundant NMR image data. The associated motion data provides an indication of the integrity of the acquired NMR image data in each set. Rather than merely averaging the redundant data, therefore, more weight is given to the NMR data with higher integrity. The result is a reduction in motion artifacts in the image which is reconstructed from the intelligently combined data.

Another object of the invention is to improve the quality of images which are reconstructed from NMR data acquired in a scan having a non-monotonic view order. The strategies which use a non-monotonic view order presume that respiration follows a smooth periodic cycle. To the extent that this is not true, the strategy does not work and motion artifacts are produced in the image. By acquiring redundant NMR data and combining it according to the teachings of the present invention, however, NMR data is produced which enhances the artifact suppressing mechanism of non-monotonic view ordered scans.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
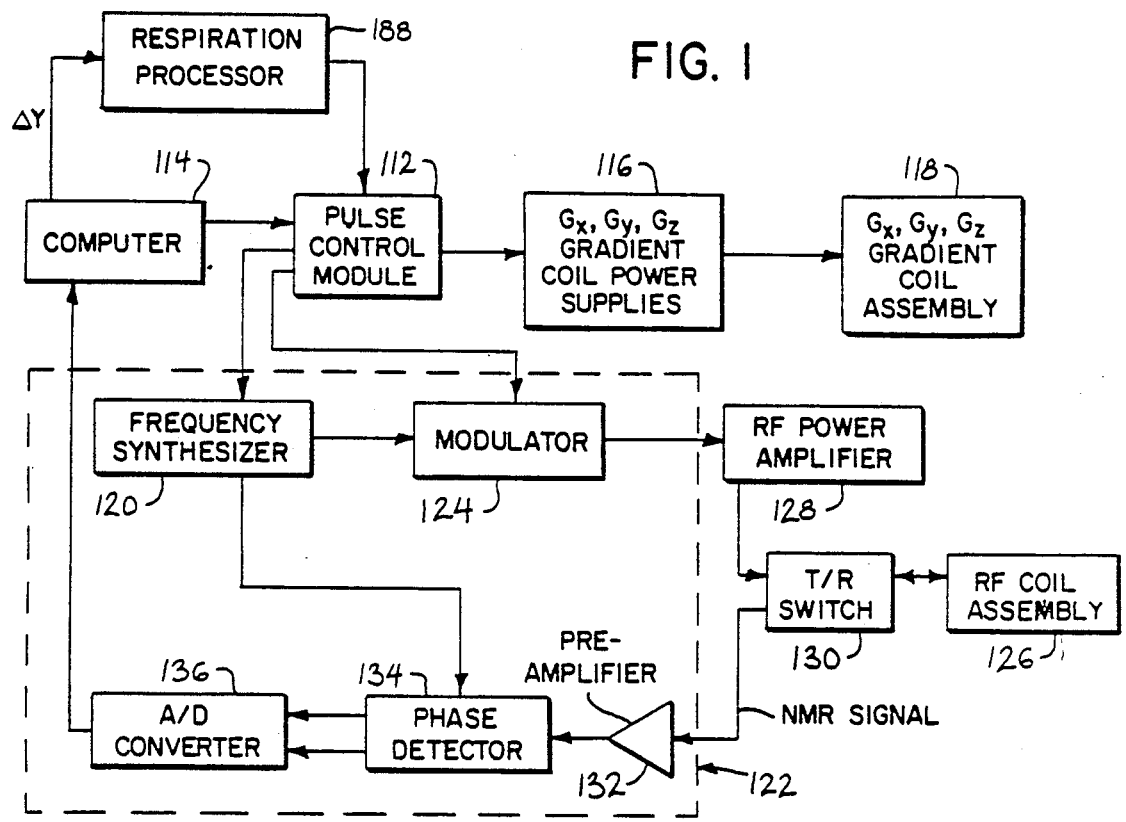
FIG. 1 is an electrical block diagram of an NMR system which employs the present invention.

FIG. 1 is a simplified block diagram of an NMR imaging system which employs the preferred embodiment of the invention. The system includes a pulse control module 112 which provides properly timed pulse waveform signals, under the control of a host computer 114, to magnetic field gradient power supplies collectively designated at 116. These power supplies 116 energize gradient coils which form part of a gradient coil assembly generally indicated by block 118. The assembly contains coils which produce the $G_x$, $G_y$ and $G_z$ magnetic field gradients directed in the x, y, and z directions, respectively, of the Cartesian coordinate system. The use of the $G_x$, $G_y$ and $G_z$ gradients in NMR imaging applications will be described hereinafter with reference to FIG. 2.

Continuing with reference to FIG. 1, the pulse control module 112 provides activating pulses to an RF synthesizer 120 which is part of an RF transceiver, portions of which are enclosed by dash-line block 122. The pulse control module 112 also supplies signals to a modulator 124 which modulates the output of the RF frequency synthesizer 120. The modulated RF signals are applied to an RF coil assembly 126 through an RF power amplifier 128 and a transmit/receive switch 130. The RF signals are used to excite nuclear spins in a sample object (not shown) which is to be imaged.

The NMR signals from the excited nuclear spins are sensed by the RF coil assembly 126 and applied through the transmit/receive switch 130 to an RF preamplifier 132. The amplified NMR signals are applied to a quadrature phase detector 134, and the detected signals are digitized by A/D converter 136 and applied to computer 114 for storage and processing.

Figure 2:
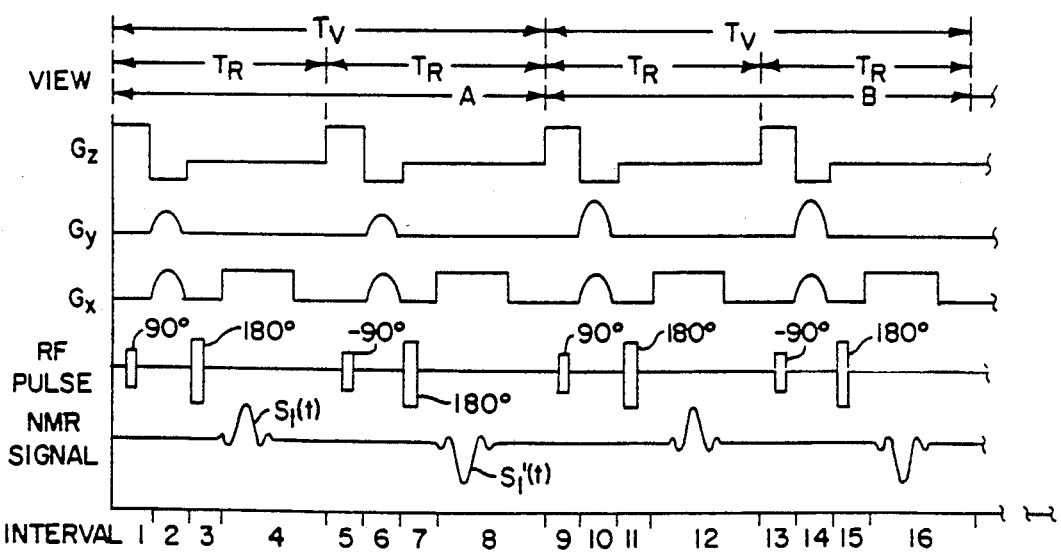
FIG. 2 is an exemplary imaging pulse sequence which is executed by the system of FIG. 1.

Reference is made to FIG. 2 which depicts two views of a conventional imaging pulse sequence of the type known as two-dimensional Fourier transforms (2DFT), and which is also referred to as two-dimensional "spin-warp". This pulse sequence is useful in obtaining, in a well known manner, imaging NMR data to reconstruct images of an object being investigated. The two views are indicated at "A" and "B" and they are identical with the exception of the phase-encoding gradient field $G_y$. Each view is a pulse sequence which utilizes phase-alternated RF excitation pulses which, as disclosed and claimed in the above-identified U.S. Pat. No. 4,443,760, produce phase-alternated NMR signals $S_1(t)$ and $S_1'(t)$ to cancel certain baseline errors in the NMR system.

Referring now to View A in FIG. 2, there is shown in interval 1 (indicated along the horizontal axis) a selective 90° RF excitation pulse applied in the presence of a positive $G_z$ magnetic field gradient pulse. Pulse control module 112 (FIG. 1) provides the needed control signals to the frequency synthesizer 120 and modulator 124 so that the resulting excitation pulse is of the correct phase and frequency to excite nuclear spins only in a predetermined region of the object being imaged. Typically, the excitation pulse can be amplitude modulated by a (sin x)/x function. The frequency of the synthesizer 120 is dependent on the strength of the applied polarizing magnetic field and the particular NMR species being imaged in accordance with the well known Larmor equation. The pulse control module 112 also applies activating signals to the gradient power supplies 116 to generate, in this case, the $G_z$ gradient pulse.

Continuing with reference to FIG. 2, $G_x$, $G_y$ and $G_z$ gradient pulses are applied simultaneously in interval 2. The $G_z$ gradient in interval 2 is a rephasing pulse typically selected such that the time integral of the gradient waveform over interval 2 is approximately equal to $—^{TM}$ of the time integral of the $G_z$ gradient waveform over interval 1. The function of the negative $G_z$ pulse is to rephase the nuclear spins excited in interval 1. The $G_y$ gradient pulse is a phase-encoding pulse selected to have a different amplitude in each of Views A, B, . . . , etc., to encode spatial information in the direction of the gradient. The number of different $G_y$ gradient amplitudes is typically selected to equal at least the number of pixel resolution elements the reconstructed image will have in the phase-encoding (Y) direction. Typically, 128, 256, or 512 different gradient amplitudes $G_y$ are selected and in the typical NMR system, the $G_y$ values are incremented a fixed amount from one view to the next until the NMR scan is complete.

The $G_x$ gradient pulse in interval 2 is a dephasing pulse needed to dephase the excited nuclear spins by a predetermined amount to delay the time of occurrence of a spin-echo signal $S_1(t)$ in interval 4. The spin-echo signal is produced typically by the application of a 180° RF pulse in interval 3. As is known, the 180° RF pulse is a pulse which reverses the direction of spin dephasing so as to produce the spin-echo signal. The spin-echo signal is sampled in interval 4 in the presence of a gradient pulse $G_x$ to encode spatial information in the direction (X) of this gradient. As indicated above, baseline error components are eliminated by using an additional NMR measurement in each view. This second measurement is substantially identical to the first with the exception that the RF excitation pulse in interval 5 of View A is selected to be 180° out of phase (as suggested by the minus sign) relative to the excitation pulse in interval 1 of View A. As a result, the spin-echo signal $S_1'(t)$ in interval 8 is 180° out of phase with the spin-echo signal $S_1(t)$ in interval 4. If the signal $S_1'(t)$ is subtracted from $S_1(t)$, only those components of the signals with reversed sign in the signal $S_1'(t)$ are retained. The baseline error components thus cancel.

The process described above with reference to View A is repeated for View B and so on for all amplitudes of the phase-encoding $G_y$ gradient. The NMR image data which is collected during this scan is stored in the host computer 114 where it is processed to produce image data suitable for controlling a CRT display.

As the above described conventional NMR scan is performed, NMR data is acquired from all physical locations within the plane, or slice, of the object being imaged. If an accurate image is to be reconstructed, then both the object and the measurement conditions must be stable, or fixed, during the time needed to complete the entire NMR scan. The present invention deals with the very practical situations in which this is not the case, but instead, the measurement conditions change in some cyclic, or nearly cyclic, manner.

One such situation occurs when an image is to be produced through the abdomen of a human subject. In this case, much of the material being imaged is in motion due to the subject's breathing, and the time needed to acquire the NMR data for an entire image will often transcend many respiration cycles. If NMR data is acquired continuously throughout the respiration cycles, the subject will be disposed differently from view to view and the reconstructed image will contain many motion artifacts.

Co-pending U.S. patent application Ser. No. 427,401 filed on Oct. 27, 1989 and entitled "A Method For Monitoring Respiration With Acquired NMR Data" describes a system in which the motion of the patient due to respiration is monitored using a special NMR pulse sequence which is interleaved with each view of the acquired image data. The disclosure of this co-pending application is expressly incorporated into this application. Referring again to FIG. 1, the motion NMR pulse sequence described in this co-pending application is executed by the pulse control module 112 just prior to the execution of each view in the image scan. The NMR signal which results is received by the computer 114 and is analyzed as described in the above cited co-pending U.S. patent application to produce a displacement value $\Delta Y$ which indicates the position of the patient's anterior abdominal wall with respect to a reference position. This displacement value $\Delta Y$ is output by the computer 114 to a respiration processor 188 which converts it in real time to a value which indicates the current phase of the patient respiration cycle. As described in the above cited U.S. Patent Nos. 4,663,591; 4,706,026 and 4,720,678, this phase value which is computed by processor 188 is applied to the pulse control module 112 to select the order in which the amplitudes of the phase-encoding gradient pulses $G_y$ are applied during the scan. In other words, the phase values produced prior to each view are used by the pulse control module 112 to control the particular non-monotonic view order which is being used to suppress artifacts caused by patient respiration. Therefore, to the extent that a phase value deviates from the true, or expected, respiration cycle of the patient, it can be anticipated that the integrity of the image data which is acquired during the subsequent view may suffer. More particularly, the motion artifact suppression strategy may be less effective and the data acquired during the subsequent view may produce more artifacts in the reconstructed image.

By using the present invention, motion artifacts can be further suppressed. As explained above, during a complete scan at least one set of image data from a digitized NMR signal is obtained at each phase encoding value, or "view number". Associated with each such set of image data is a displacement value $\Delta Y$ which indicates the measured respiration phase when the NMR image data set was acquired. In addition, it is also possible to obtain more than one set of NMR image data and an associated displacement value ΔY for each view number. For example, the pulse sequence of FIG. 2 can be executed twice for each phase encoding value during the scan, or a second scan can be executed. In either case, redundant NMR image data is acquired and may be combined to reduce noise and motion artifacts in accordance with the present invention.

It is, of course, common practice to combine redundant NMR image data to reduce random noise. Such a combination is accomplished by taking the average value of the corresponding data elements in each array of acquired image data. For example, if two values for each element have been acquired, their values are added and the result is divided by two. Such averaging provides a $\sqrt{2}$ reduction in random noise. This well known method weights each value equally in arriving at the average.

The present invention combines redundant NMR data to improve image quality, but it weights the acquired values being combined as a function of their measured integrity. As will now be explained in detail, the integrity of the NMR data is measured by using the associated displacement values ΔY.

Figure 3:
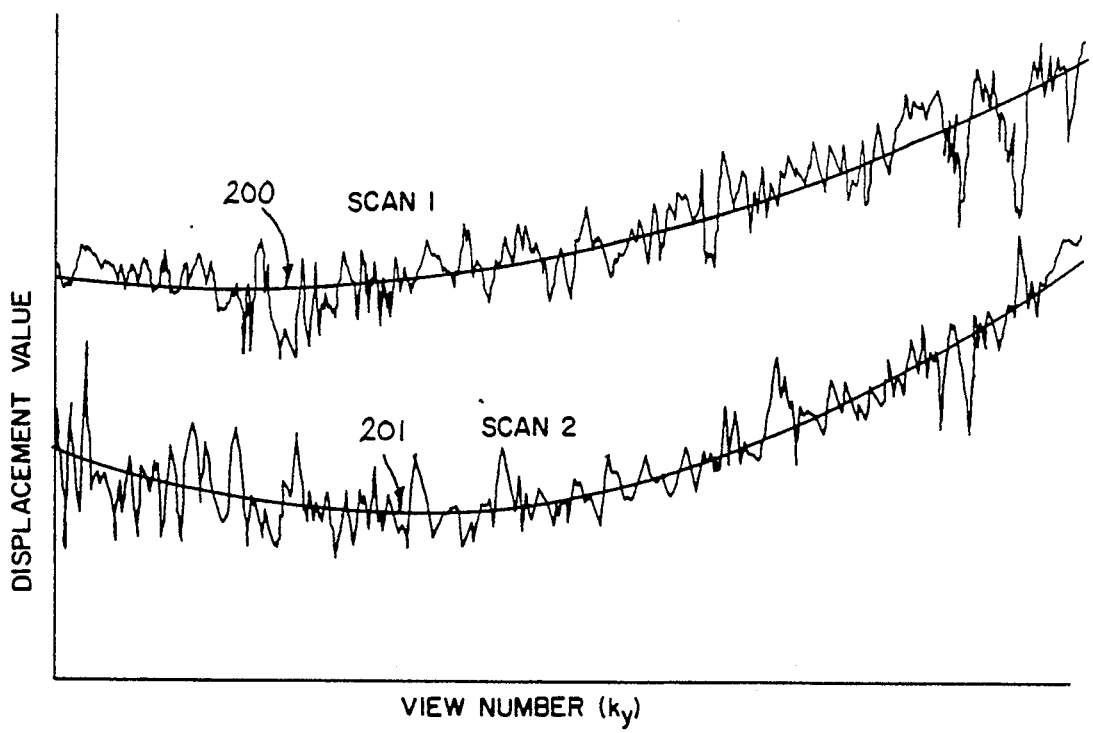
FIG. 3 is a preferred embodiment of the motion phase pulse sequence which is interleaved with the imaging pulse sequence of FIG. 2.

Referring particularly to FIG. 3, the displacement values ΔY for each view in two successive scans are plotted. A "low frequency" sort as described in the above cited U.S. Pat. Nos. 4,663,591; 4,706,026 and 4,720,678 was used to acquire the associated image data, and as a result, the measured displacement values should follow a slowly changing smooth curve as indicated at 200 and 201. It is readily apparent that the displacement values deviate from these smooth curves, and it is a teaching of the present invention that the extent of this deviation is an indication of the propensity for motion artifact generation when the associated image data is used to produce an image. Such deviations, therefore, provide a quantitative measure of the integrity of the image data. It should be noted that these deviations are not necessarily measurement errors, but may instead be caused by spurious variations in the patient's breathing pattern which has disrupted the motion artifact suppression strategy. Accordingly, the present invention combines the redundant NMR image data to reduce both noise and motion artifacts by weighting the data as a function of the deviations in their corresponding displacement values.

Figure 4:
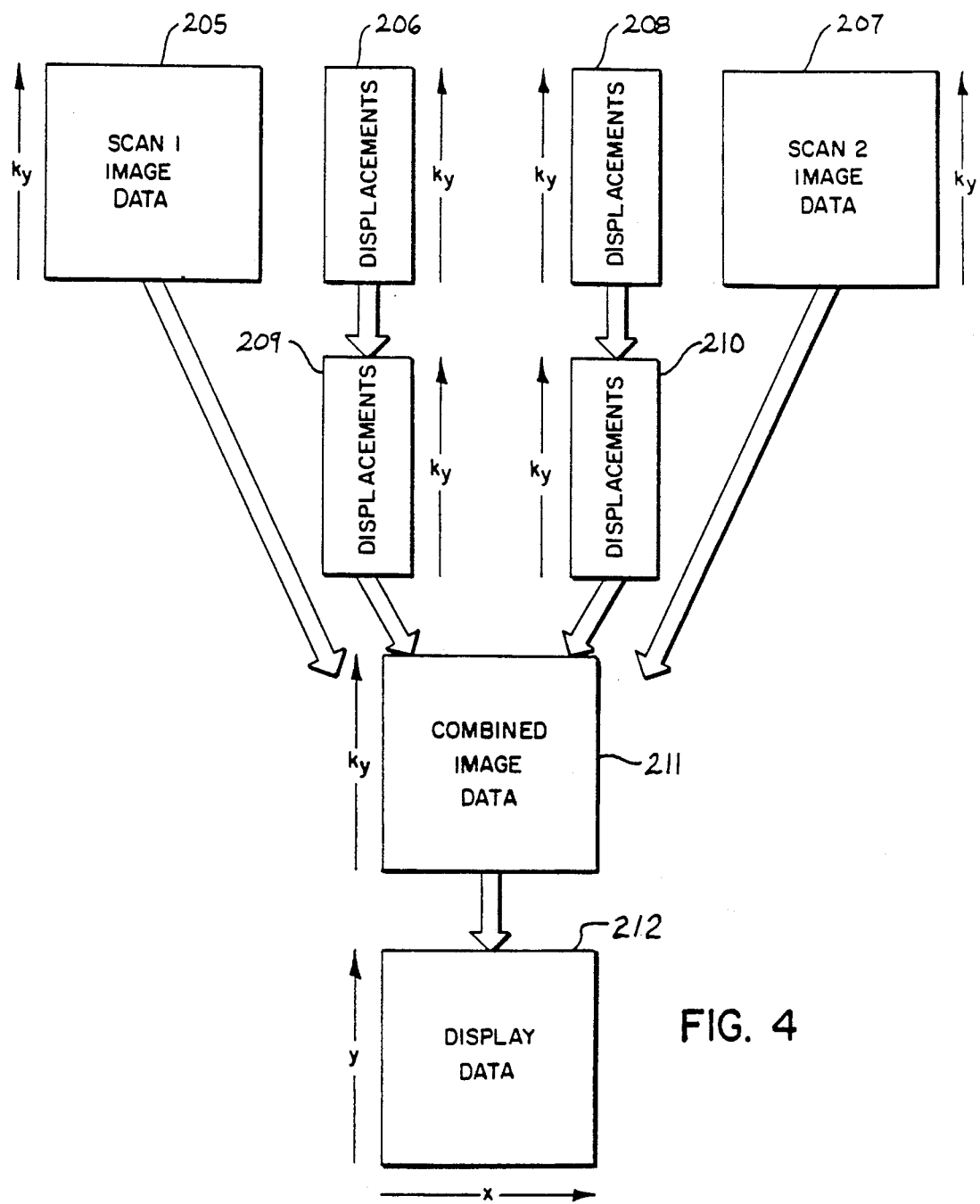
FIG. 4 is a pictorial representation of the data structures which are produced when practicing the preferred embodiment of the invention.

The invention is carried out by the computer 114 under the direction of a program which is executed after the data sets have been acquired. The operation of this program will now be described with reference to the flow chart in FIG. 5. As indicated in FIG. 4, the acquired data includes a two-dimensional array of image data 205 and an associated one-dimensional array 206 of displacement data such as that illustrated in FIG. 3. Similar arrays 207 and 208 are stored for the second scan, or second set of acquired NMR data. The image data and the associated displacement data have been sorted into sequential view number order, with each row of image data array 205 and 207 being associated with a corresponding element in its respective displacement array 206 and 208.

Figure 5:
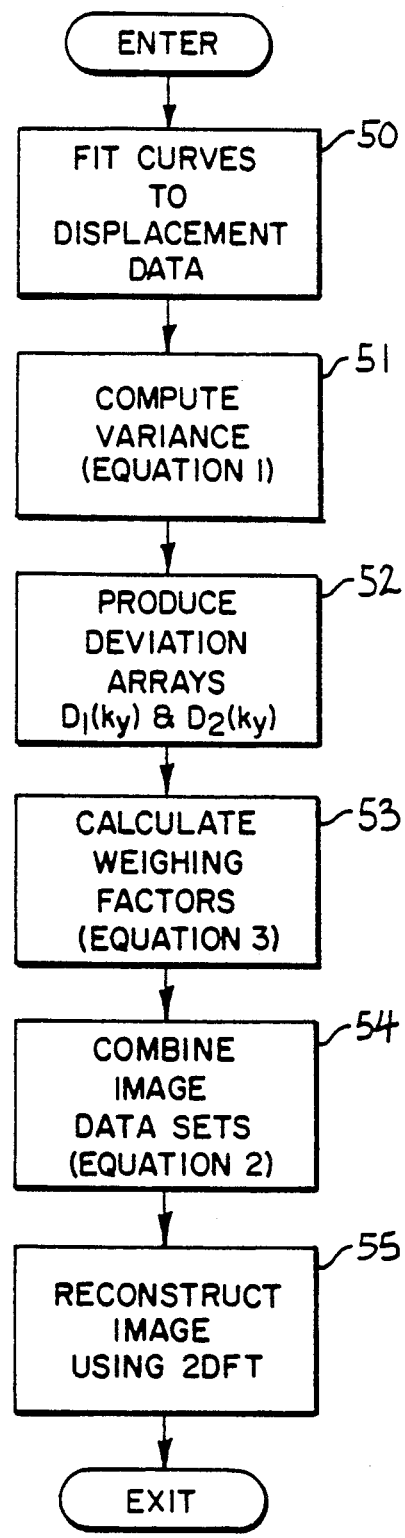
FIG. 5 is a flow chart of a program executed by the NMR system of FIG. 1 to carry out the present invention.

As indicated by process block 50 in FIG. 5, the first step of the processing is to fit a quadratic equation to the values in the displacement arrays 206 and 208 using a well known least-squares technique. This effectively establishes the smooth curves 200 and 201 (FIG. 3) which serve as the reference from which deviation values can be computed. These are identified as reference functions $r_1(k_y)$ and $r_2(k_y)$. As indicated by process block 51, the scan with the smallest variance in displacement values from their reference curve is then computed as follows:

$$\text{Variance} = (1/N) \sum_{k_y=1}^{N} (m(k_y) - r(k_y))^2 \quad (1)$$

where:
N the total number of views in the scan,
$m(k_y)$ values in the displacement array, and
$r(k_y)$ values of the reference function.

Absolute deviations between the displacement values $m(k_y)$ and their reference values $r(k_y)$ are then calculated subject to a lower threshold deviation δ (0.003 in the preferred embodiment), as indicated by process block 52. That is, one-dimensional deviation arrays 209 and 210 are produced by finding the absolute value of the difference $m(k_y) - r(k_y)$. If the difference does not exceed the threshold value (δ), then the corresponding image data elements are weighted equally (i.e., 0.5).

Using the deviation values $D_1(k_y)$ and $D_2(k_y)$ in the respective arrays 209 and 210, the image data in the arrays 205 and 207 is now combined. More specifically, each row of data $S_1(k_y)$ in the first image data array 204 is combined with its corresponding row of data $S_2(k_y)$ in the second image data array 207 to form a row of data $S(k_y)$ in a combined image data array 211 as indicated by process blocks 53 and 54.

$$S(k_y) = S_1(k_y)(W_1(k_y)) + S_2(k_y)(W_2(k_y)) \quad (2)$$

where:

$$W_1(k_y) = D_2(k_y)/(D_1(k_y) + D_2(k_y)) \quad (3)$$

$$W_2(k_y) = D_1(k_y)/(D_1(k_y) + D_2(k_y))$$

As indicated above, the weighting factors $W_1$ and $W_2$ are set equal to 0.5 in cases where both deviations are less than the threshold amount (δ).

The resulting image data array 211 is then processed as indicated at block 55 using the conventional reconstruction technique (2DFT in the preferred embodiment) to produce a two-dimensional display data array 212 which indicates the intensity of each display pixel.

It should be apparent to those skilled in the art that while two sets of data are acquired in the preferred embodiment of the invention, the invention is also applicable when three or more sets of data are acquired. Regardless of the number of sets acquired, the present invention can be employed to select the best data or to weight the averaging of the data to minimize motion artifacts.

We claim:

1. An NMR system for producing an image of a subject undergoing motion, the combination comprising:
   means for acquiring a plurality of sets of NMR image data;
   means for acquiring with each set of image data an associated set of motion data that indicates motion of the subject during each view of acquired image data;
   means for generating a smooth reference curve for each set of acquired motion data;
   means for determining the deviation of the acquired motion data from a reference curve; and means for combining each view in the sets of NMR image data by weighting the NMR image data as a function of the deviation of its associated motion data.

2. The NMR system as recited in claim 1 in which the means for acquiring the sets of motion data includes means for producing a motion NMR pulse sequence and the means for acquiring the sets of NMR image data includes means for producing an image NMR pulse sequence; and each of said data sets is acquired in a scan comprised of a plurality of image NMR pulse sequences interleaved with a plurality of the motion NMR pulse sequences.

3. The NMR system as recited in claim 2 in which the motion data in each set indicates the displacement of a feature in the subject from a reference position, and the smooth reference curve is generated by fitting a curve to the displacement values in the motion data set.

4. The NMR system as recited in claim 3 in which the means for combining each view weights the NMR image data in each set inversely proportional to the magnitude of the deviation of its associated motion data from the reference curve.

5. The system as recited in claim 1 in which two sets of NMR image data $S_1(k_y)$ and $S_2(k_y)$ are acquired along with two sets of associated motion NMR data, the means for determining deviation produces two sets of deviation data $D_1(k_y)$ and $D_2(k_y)$, and the means for combining each view in the sets of NMR image data performs the following calculations:

$$S(k_y) = S_1(k_y)(W_1(k_y)) + S_2(k_y)(W_2(k_y));$$

where:

$$W_1(k_y) = D_2(k_y)/(D_1(k_y) + D_2(k_y));\text{ and}$$

$$W_2(k_y) = D_1(k_y)/(D_1(k_y) + D_2(k_y)).$$

* * * * *